US012603181B1

(12) United States Patent
Johnson

(10) Patent No.: US 12,603,181 B1
(45) Date of Patent: Apr. 14, 2026

(54) SYSTEM AND METHOD FOR PROVIDING DENTAL SERVICES TO A PATIENT

(71) Applicant: Andrew Johnson, Fayetteville, AR (US)

(72) Inventor: Andrew Johnson, Fayetteville, AR (US)

( * ) Notice: Subject to any disclaimer, the term of this patent is extended or adjusted under 35 U.S.C. 154(b) by 0 days.

(21) Appl. No.: 18/819,419

(22) Filed: Aug. 29, 2024

Related U.S. Application Data

(63) Continuation-in-part of application No. 18/597,125, filed on Mar. 6, 2024, which is a continuation-in-part of application No. 16/575,211, filed on Sep. 18, 2019, now abandoned.

(60) Provisional application No. 62/839,331, filed on Apr. 26, 2019.

(51) Int. Cl.
| | |
|---|---|
| *G16H 50/20* | (2018.01) |
| *A61C 13/01* | (2006.01) |
| *A61C 13/08* | (2006.01) |
| *A61C 13/10* | (2006.01) |
| *A61C 13/107* | (2006.01) |
| *A61C 13/34* | (2006.01) |

(52) U.S. Cl.
CPC ......... *G16H 50/20* (2018.01); *A61C 13/0001* (2013.01); *A61C 13/01* (2013.01); *A61C 13/08* (2013.01); *A61C 13/10* (2013.01); *A61C 13/34* (2013.01)

(58) Field of Classification Search
CPC ...... G16H 50/20; A61C 13/0001; A61C 13/01
See application file for complete search history.

(56) References Cited

U.S. PATENT DOCUMENTS

| | | | |
|---|---|---|---|
| 6,398,548 B1 | 6/2002 | Muhammad et al. | |
| 7,077,646 B2 | 7/2006 | Hilliard | |
| 7,523,044 B2 | 4/2009 | Rosenblood | |
| 10,179,035 B2 | 1/2019 | Shivapuja et al. | |
| 2008/0001572 A9 | 1/2008 | Dunne et al. | |
| 2008/0015727 A1* | 1/2008 | Dunne ................... | B33Y 30/00 |
| | | | 700/118 |
| 2009/0287332 A1* | 11/2009 | Adusumilli ............ | B33Y 50/00 |
| | | | 700/118 |
| 2012/0179281 A1* | 7/2012 | Steingart ................ | A61C 13/10 |
| | | | 703/11 |
| 2013/0108988 A1* | 5/2013 | Simoncic ........... | A61C 13/1016 |
| | | | 700/98 |
| 2015/0156208 A1 | 6/2015 | Kirkham et al. | |
| 2017/0281313 A1 | 10/2017 | Kim et al. | |

* cited by examiner

*Primary Examiner* — Evangeline Barr
(74) *Attorney, Agent, or Firm* — Wright Lindsey Jennings, LLP; Meredith Lowry

(57) ABSTRACT

A system and method providing a dental patient user interface to allow a patient to accurately scan existing patient dentures to provide a digital image for use by a provider to assess the needs and interests of the patient prior to a visit to then provide treatment facilitating/smile preview devices for use at the initial visit.

7 Claims, 10 Drawing Sheets

SYSTEM AND METHOD FOR PROVIDING DENTAL SERVICES TO A PATIENT

CROSS-REFERENCE TO RELATED APPLICATIONS

This application claims priority to and is a continuation-in-part of U.S. application Ser. No. U.S. application Ser. No. 18/597,125, filed Mar. 6, 2024, which claims priority to and is a continuation-in-part of U.S. application Ser. No. U.S. application Ser. No. 16/575,211, filed Sep. 18, 2019, which claims priority to and is a continuation-in-part of U.S. application Ser. No. U.S. application 62/839,331, filed Apr. 26, 2019, the entireties of which are hereby incorporated by reference.

FEDERALLY SPONSORED RESEARCH AND DEVELOPMENT

Not applicable.

BACKGROUND OF THE INVENTION

The invention is related generally to the field of prosthodontics, but allows similar applications in cosmetic dentistry, orthodontics, maxillofacial and peridontonal surgery as well. More particularly, the present invention is related to a method and system for providing and facilitating access to digital prosthetic smile design through use of a digital platform that defines patient expectations, establishes provider patient-provider relationships, conveys initial information and produces physical devices for the efficient completion of the dental procedures which achieves those pre-designed treatment goals.

SUMMARY OF THE INVENTION

The process for obtaining dental treatment, namely prosthodontic and surgical services like dentures and/or dental implants can be a daunting process for patients and providers. For patients, the selection of a qualified provider can be confusing, and the effort and expense of the consultative/diagnostic process can be discouraging especially when the professional opinions acquired do not align with initial patient expectations. For a provider, the process of scheduling, meeting, assessing, and reviewing the needs of a prospective new patient in order to propose treatment and discuss the procedural steps can be an expense of time that the provider is unsure will pay off. Furthermore, when a patient and a provider do align on a treatment goal and the associated procedural plan, there are several preliminary steps (notably the primary dental molds and initial smile design process, and the production of recording devices and prosthetic appliances) that then must occur. While these steps allow for visualization and accuracy in developing and delivering expected results, they add significant time and expense to the overall treatment process. There is a need, therefore, to streamline the process while additionally providing informational and educational benefits to patients and providers respectively.

Currently, when a patient, Patient A, needs dentures, Patient A must either be referred to a dental provider or find one through directories. Patient A must then schedule and attend an initial consult and/or examination. Anyone who has sought a new doctor or dentist knows that initial consults are fraught with idle chitchat, leading to lost time by both the patient and the provider. However, the initial consult is important because Patient A must at least receive a cursory, visual assessment and have a discussion about general problems and tentative treatment options. Patient A, if she is satisfied with the provider and the treatment proposed, will then return to the dental clinic for a series of separate appointments required to accomplish all the procedural steps in creating a denture, traditionally beginning with preliminary molds of her mouth. The additional steps in the traditional denture workflow along with the usual gap between initial consult and molds can contribute to more lost time and even an opt-out or loss of customer by the provider. Only towards the end of the usual four to seven appointment process is a try-in model of the final denture available for fitting and viewing. Patient A and the doctor must review and approve the try-in to make sure Patient A and the doctor are satisfied with the appearance and the function of the dentures. If adjustments have to be made, Patient A may require another visit for a later review of the corrected try-in. Once the doctor and Patient A are satisfied, then the dentures can be completed.

In contrast, the proposed invention is a platform accessible through a computing device by a patient that provides a directory of approved dental providers. Patient B, upon accessing the portal, can upload photographs and/or videos of her mouth, face, smile and existing dental prostheses for review by both a dental laboratory and selected providers in her preferred area of service. Involvement by the dental laboratory at this stage is atypical, but important to provide the initial dental assets for the first appointment with the patient. Initially the dental laboratory service provides the digital smile design preview in terms of modified versions of the submitted patient images. If the patient is interested in identifying and pursuing the actual dental treatment necessary to achieve that previewed smile in reality, they are then asked to prioritize their most desired dental provider attributes and rank their preferred provider selections from the list in the platform database. The providers, once presented with the images, patient information as well as the smile design preview can opt to provide service or decline service to the patient. Patient B can then agree to schedule an initial appointment with the accepting provider. Since the provider has seen Patient B's images and associated case information prior to the initial meeting, the initial appointment can more directly and visually address the patients desires rather than awkward chitchat followed by generalized and potentially discouraging professional opinions in terms of appropriate procedures, cost, timelines, etc. With the digital images already available, the provider can then have a digital image of the prospective change to Patient B's smile for presentation to Patient B in the first meeting as well as a preemptive opportunity to offer rough cost estimates, procedural complexity and treatment timelines. With the digital images provided to the dental laboratory ahead of the clinical diagnostic appointment, the dental laboratory can prepare initial dental assets for review by the provider and ship these assets to the provider for use at the initial meeting. This upfront information supplemented with a potential treatment result visualization, will give Patient B more ability to decide if the selected provider is best suited to accomplish her treatment goals, and Patient B is more likely to present for the initial visit prepared to move forward with the treatment, thus reducing the risk of the provider losing time. In this manner, the proposed invention enhances the quality of communication and reduces lost time for both the patient and the provider thereby increasing the value of the entire interaction for both parties.

In addition to the digital smile preview and preemptive two-party case approval and treatment information provided, for applicable treatment categories (like dentures, orthodontics, implants, esthetics, etc.), the approved digital smile design preview can be produced as physical objects via prototyping technologies like three-dimensional printing and utilized in the course of actual in-person diagnostics and treatment procedures. Physical recording devices, smile try-ins, and/or prosthetic appliances can be produced ahead of the initial appointment and made available to the patient and/or the selected provider for direct use/visualization in the first appointment. By incorporating three-dimensional scan data acquired at a participating scanning/diagnostic center with the patient photographs, a three-dimensional digital smile design can be completed and converted to physical media for use in the actual course of diagnostics and treatment. The early generation and implementation of such physical treatment renderings (smile try-ins), recording devices (impression trays, bite registrations, etc.), or even prostheses like dentures so to allow for direct viewing at the front end of the patient-provider interaction can lead to more motivated patients as well as more a predictable and efficient treatment process. Furthermore, given the unique manner of managing a wide range of initial data quality as described in this process (i.e. relatively low resolution, improperly scaled photos/videos of ill-fitting, unesthetic dentures), the initial three-dimensional data necessary to preemptively design the physical treatment assets/devices can be created not only from high-quality data acquired by dedicated dental scanning devices or even off-label hobbyist 3D scanners, but from the initially submitted two-dimensional photos/videos themselves. The ability to acquire and submit the intake diagnostic data directly from a patient's smartphone alone, without requiring the use of specialized accessories, applications, or devices and then use that basic digital information to not only propel the smile-design process and initial patient-provider connection/communication, but to also create the pre-produced physical recording, try-in, and prosthetic devices used in the course of the in-person procedures is a huge benefit to the efficiency and appeal of the entire diagnostic and treatment process.

These and other objects, features, and advantages of the present invention will become better understood from a consideration of the following detailed description of the preferred embodiments and appended claims in conjunction with the drawings.

DETAILED DESCRIPTION OF THE INVENTION

Figure 1:
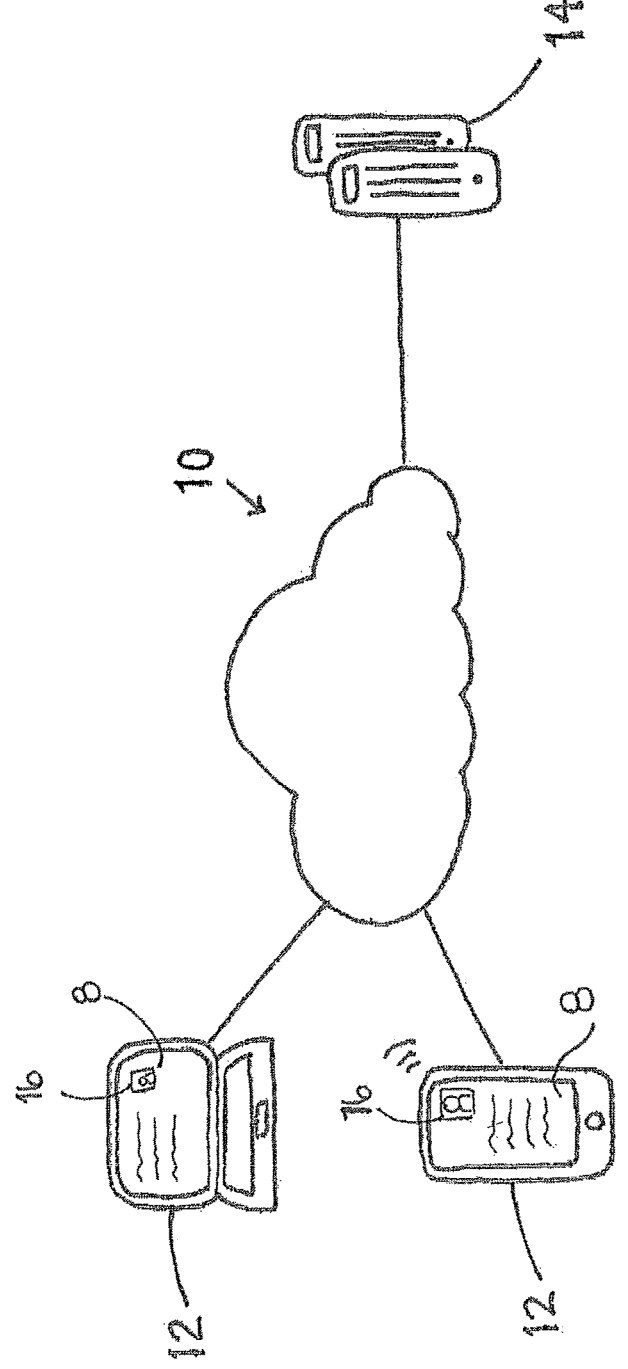
FIG. 1 is a schematic of the method of the present invention.

Generally speaking, the present invention is directed to a system and method for directing an personal computing device or mobile device user in need of smile-enhancing dentistry to find, evaluate and select a provider for dental services (namely dentures, crowns, veneers, dental implants, orthodontics, periodontics, and/or maxillofacial surgery), motivate her to pursue the predicted visual treatment results, inform her on issues related to achieving those results (i.e. costs, timeframes, procedures, etc.), then produce and provide physical devices that facilitate the treatment planning and procedural process. Specifically, the present invention is a platform that allows a user to evaluate and request services from network providers while streamlining the process for the dentist.

"Artificial intelligence" as used herein to broadly describe any computationally intelligent systems that combine knowledge, techniques, and methodologies. An AI engine may be any system configured to apply knowledge and that can adapt itself and learn to do better in changing environments. Thus, the AI engine may employ any one or combination of the following computational techniques: neural network, constraint program, fuzzy logic, classification, conventional artificial intelligence, symbolic manipulation, fuzzy set theory, evolutionary computation, cybernetics, data mining, approximate reasoning, derivative-free optimization, decision trees, and/or soft computing. Employing any computationally intelligent techniques, the AI engine may learn to adapt to unknown and/or changing environment for better performance.

The present application refers to image processing of images (e.g. pictures, figures, graphical schematics, single frames of movies, videos, films, clips, etc.) captured by cameras, especially cameras of mobile devices. As understood herein, a mobile device is any device capable of receiving data without having power supplied via a physical connection (e.g. wire, cord, cable, etc.) and capable of receiving data without a physical data connection (e.g. wire, cord, cable, etc.). Mobile devices within the scope of the present disclosures include exemplary devices such as a mobile telephone, smartphone, tablet, personal digital assistant, iPod®, iPad®, BLACKBERRY® device, etc.

As used herein, the term "computing device," refers to a device including a processing unit and having computing capabilities. Some examples of a computing device include a PC, laptop, tablet, or a mobile device having a display. The computing device may be coupled, connected, and/or in communication with a network via communication channels including, but not limited to Internet connections, satellite communications, wireless channels, cloud connections, etc.

As used herein, the term database refers to an organized collection of data with a software system designed to allow the definition, creation, querying, update, and administration of databases.

The term patient encompasses, but is not limited to, a recipient of health care services.

As used herein, the term platform refers to a computer software application hosted on a server, stored persistently on storage or memory available to the server, and executing on one or more computing devices of the server.

As used herein, the term server refers to a system (software and suitable computer hardware) that responds to requests across a computer network.

The present invention is represented by the Internet-accessible platform 8 allowing a patient to review the database of providers for dental services through use of a computing device 12. The network 10 represents the communication pathway between the patients' computing devices 12 and the online system stored on one or more servers 14. In one embodiment, the network 10 is the internet. The network 10 can also utilize dedicated or private communication links (e.g. WAN, MAN, or LAN) that are not necessarily part of the Internet. The networked patient devices 12 use standard communication technologies and/or protocols.

The patient computing devices 12 are used by the patients interacting with the online platform system 8. The device 12 executes an operating system, for example, a Microsoft Windows-compatible operating system (OS), Apple OS X or iOS, a Linux distribution, or Google's Android OS. In some embodiments, the device 12 may use a web browser, such as Microsoft Internet Explorer, Mozilla Firefox, Google Chrome, Apple Safari and/or Opera, as an interface to interact with the online platform. In other embodiment, the device 12 can execute a dedicated application for accessing the online platform 8.

The online platform 8 includes a server 14 that presents web pages or other web content, which form the basic interface to the patients. Patients use respective devices 12 to access one or more web pages, and provide data to the system through the online platform 8.

The online platform 8 may be for example a scheduling system, a treatment analysis system, a provider referral system, a patient education system, a provider education system, a 2D/3D image viewer, and a third party payer verification/preauthorization system and the like. In some embodiments, the online platform 8 facilitates transactions between the patient and the provider. For example, a scheduling system allows patients to request appointments for dental consultation with the provider or the treatment analysis system provides patient images for processing by the system and analysis by the provider to initiate treatment of the patient. The present invention focuses on the treatment system and hereafter the term "system" will refer to this portion of the invention.

Those of skill in the art will appreciate that the system will contain other modules appropriate for its functionality (e.g., social networking, banking, commerce, etc.), but that are not described herein, since they are not directly material to the invention. In addition, conventional elements, such as firewalls, authentication and encryption systems, network management tools, load balancers, and so forth are not shown as they are not material to the invention. The system may be implemented using a single computer, or a network of computers, including cloud-based computer implementations. The computers are preferably server class computers including one or more high-performance computer processors and main memory, and running an operating system such as LINUX or variants thereof. The operations of the system as described herein can be controlled through either hardware or through computer programs installed in non-transitory computer storage and executed by the processors to perform the functions described herein. The database is implemented using non-transitory computer readable storage devices, and suitable database management systems for data access and retrieval. The database is implemented in a database management system, such as a relational database (e.g., MySQL). The system includes other hardware elements necessary for the operations described here, including network interfaces and protocols, input devices for data entry, and output devices for display, printing, or other presentations of data. As will become apparent below, the operations and functions of the system are sufficiently complex as to require implementation on a computer system, and cannot be performed as a practical matter in the human mind.

Figure 2:
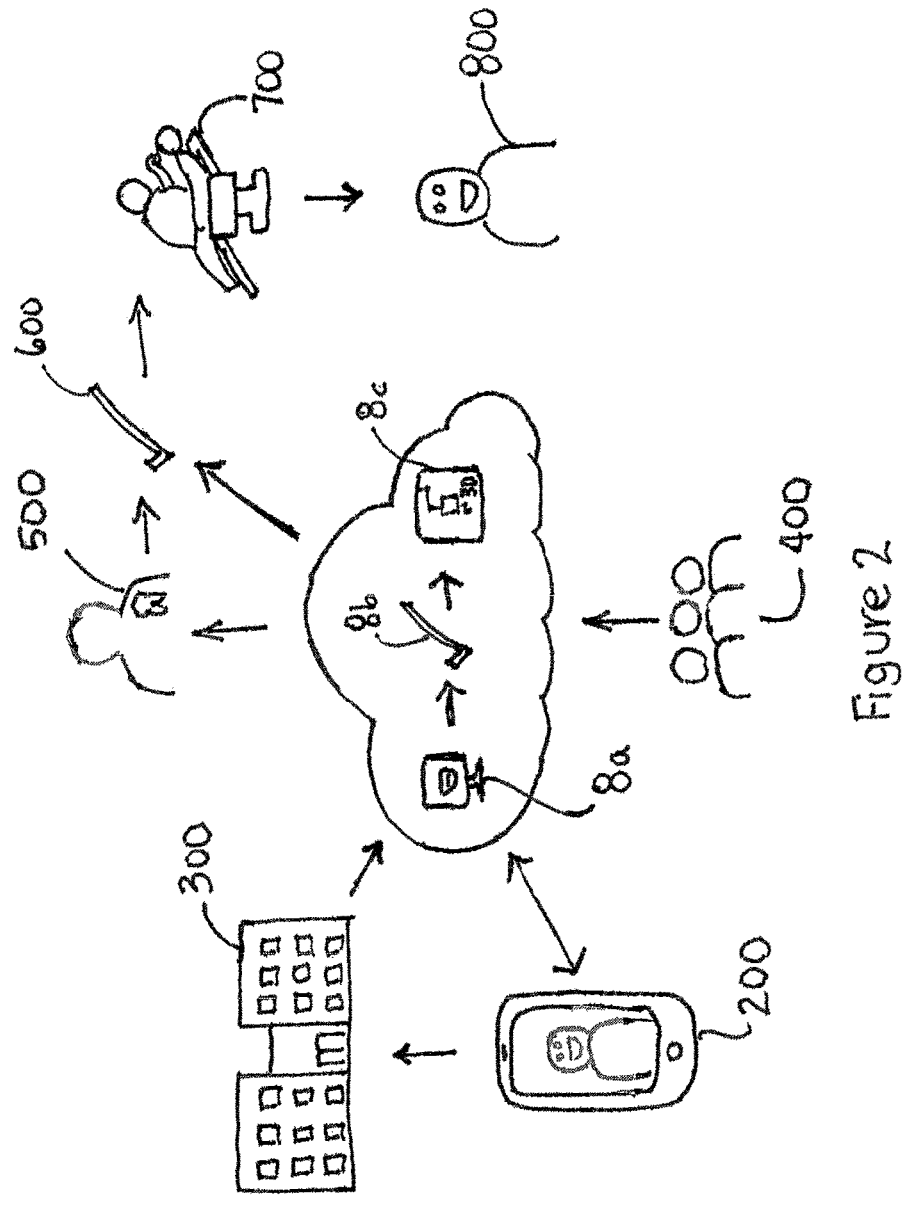
FIG. 2 is a schematic of the method of the present invention.
Figure 3:
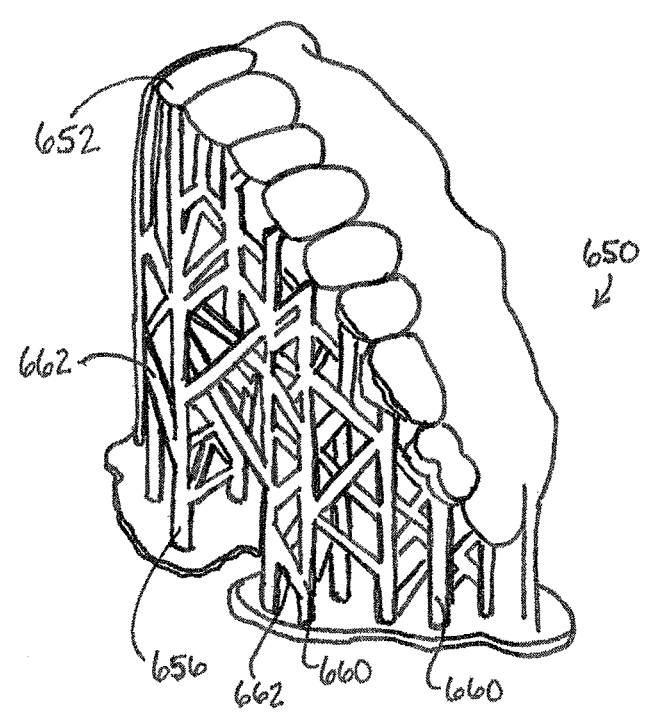
FIG. 3 is a perspective view of an embodiment of the present invention.
Figure 4:
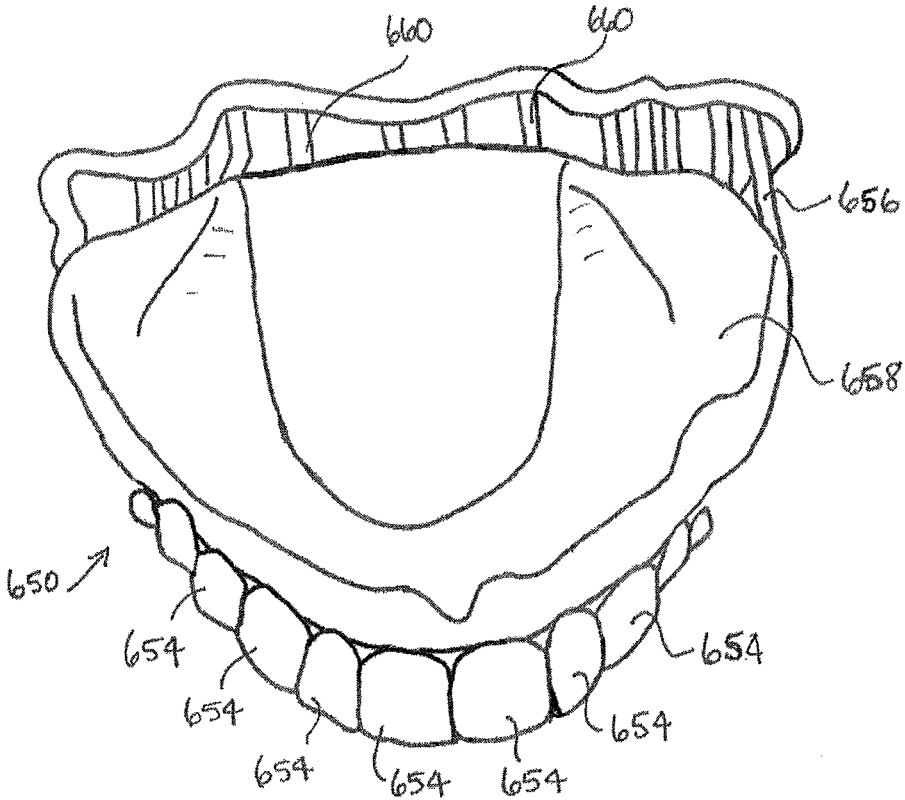
FIG. 4 is a top view of an embodiment of the present invention.
Figure 5:
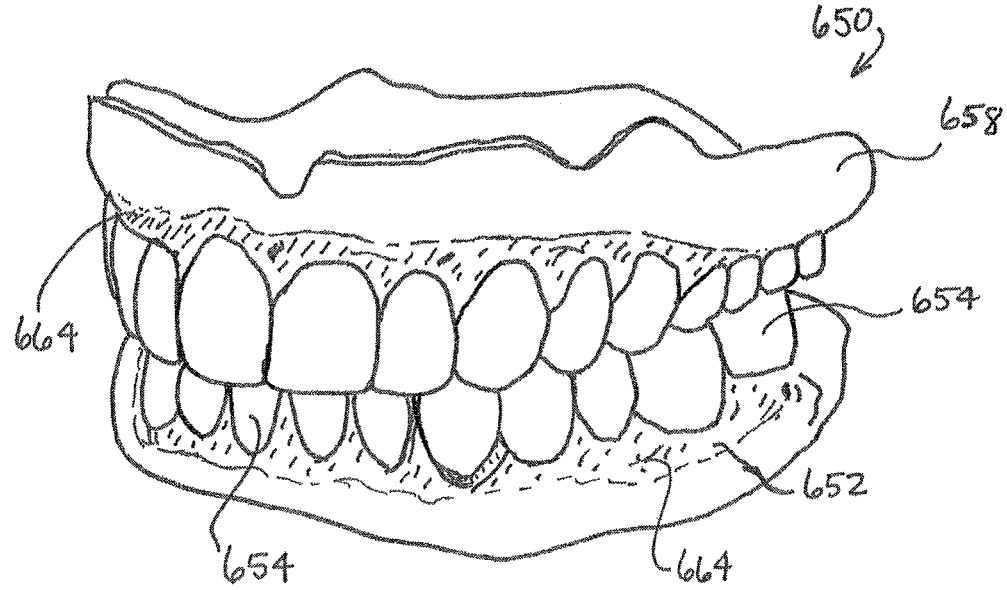
FIG. 5 is a front view of an embodiment of the present invention.

As detailed in FIG. 2, the system provides a patient interface and processing logic for a patient to provide an image capture of the patient's face and teeth utilizing the patient's mobile device 12. The user interface may use prompts, such as a screen image in the interface that requests that the patient place the patient's face within the screen image for the image capture. The uploaded digital images 40 of the patient can be captured 200 through a camera module on the user mobile device or through an upload module. The user interface provides prompts to the patient accessing the user interface to provide 200 a facial image showing the face of the patient from multiple angles, including a front-facing image of the of the patient and a perspective view of the patient face to provide image data for the system to generated images for treatment of the patient.

Additionally, the system may contain an artificial intelligence engine to aid in determining and/or identifying if the uploaded digital image of the patient does not meet the requirements of the system, namely if the uploaded digital image does not capture the whole face or does not show the teeth of the patient. The artificial intelligence engine may prompt the patient immediately after upload or at a later time to then request images to be uploaded to the system. The artificial intelligence engine could also propose an immediate digital smile preview through the use of facial tracking and augmented reality for initial patient visualization/motivation purposes.

Once the uploaded digital image is verified as a correct submission, the system utilizes an artificial intelligence engine to calculate patient information from the uploaded digital image, namely smile-design related facial landmarks of the patient.

Figure 6:
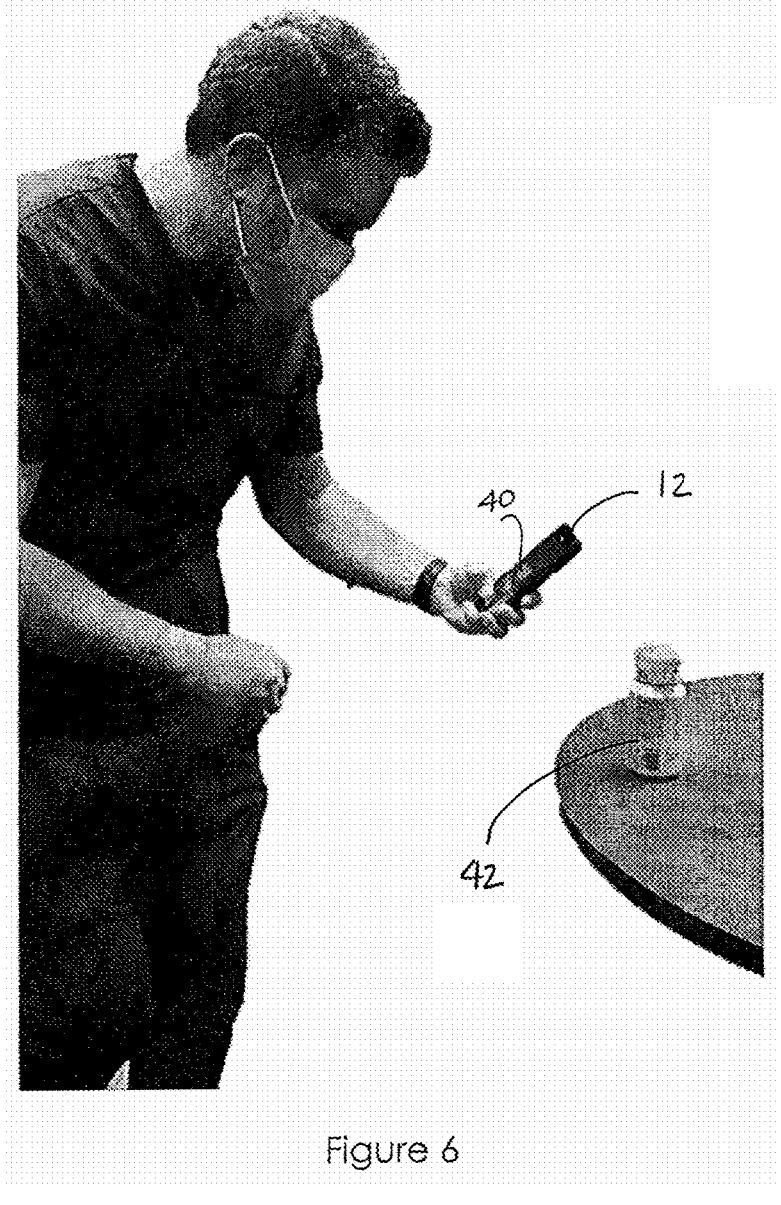
FIG. 6 is an image of a person scanning a set of dentures as part of the present invention.
Figure 7:
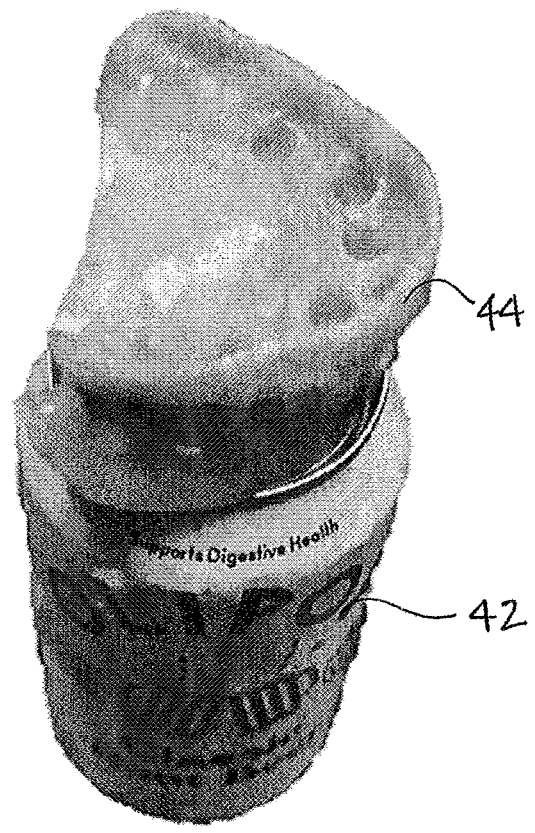
FIG. 7 is an image of a set of dentures for scanning and a representative scale object.

In an embodiment of the present invention, the system prompts the patient to include additional digital media files, such as image capture files or video files of the patient's existing dentures on top of a common household object to provide scale context for the images or videos. As shown in FIG. 6, the present invention utilizes the patient's mobile device 12 to capture the images or video 40 of the patient's existing dentures 44. As shown in a larger image in FIG. 7, the preferred scale object 42 for the present invention is an aluminum soda can as many households contain this scale object 42 and it is relatively consistent in its known dimension. In a preferred embodiment, the system prompts the patient to use the camera of the mobile device 12 to capture a circumferential video of the existing dentures.

Figure 8:
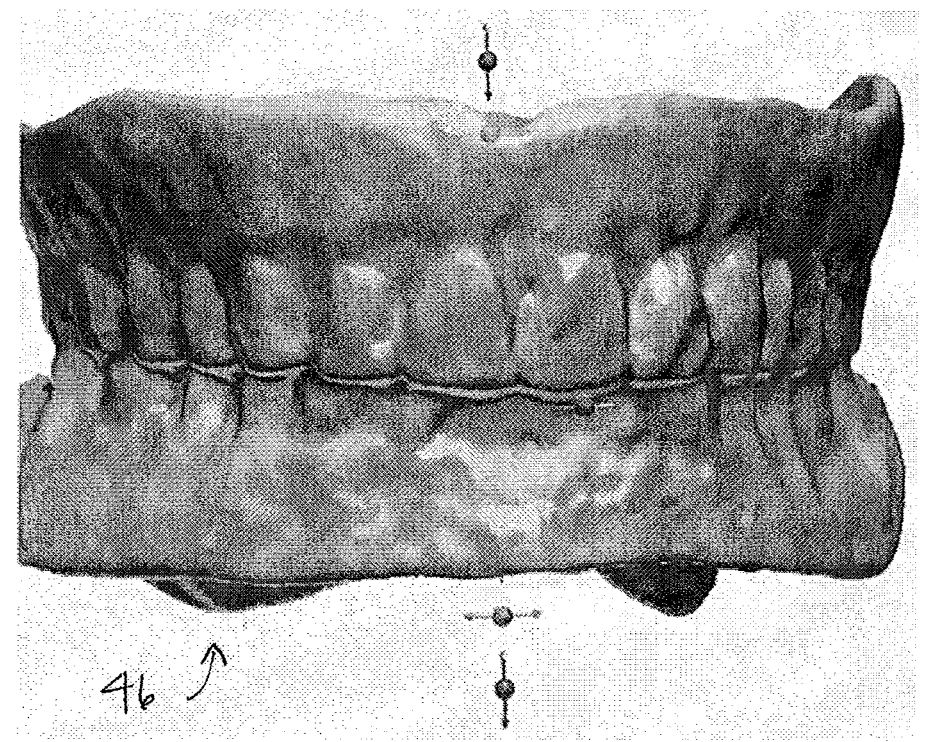
FIG. 8 is an initial scan of current dentures for a patient.

Once the captured video is uploaded to the system, the system processes the video to render three-dimensional images 46 of the dentures which are then properly scaled relative to the reference object 42 (i.e. the soda can). In a preferred embodiment of the present invention, the system utilizes artificial intelligence processing to process the video images to render three-dimensional scans of the dentures. An example of the rendering processing tool utilized by the present invention is AI Scanner, provided by MakerWorld Singapore Pte. Ltd. (a/k/a Bambu Lab) of Singapore. A rendered three-dimensional image of a set of dentures is shown in FIG. 8. The system allows rotation and manipulation of the rendered 3D image data to allow for the provider to assess the case prior to acceptance of the appointment as well as for the lab to complete the design and production of the physical assets prior arrival of the patient for the first clinical appointment.

Subsequent to the submission of initial patient video data (acquired and submitted by the patient 200) through the platform, processing of patient video data to produce background patient data 48, such as jaw structure 49 and rendering three-dimensional images of patient dentures, a provider may initiate a digital smile design process. As shown in FIGS. 9-12, the system allows the initial 3D denture rendering to be utilized to create additional 3D object renderings to produce a digital smile preview 8a for review by the patient 200 for initial approval 8b. In another embodiment, the system provides a tool for rendering initial dental assets 8c prior to any clinical dental appointment.

Figure 9:
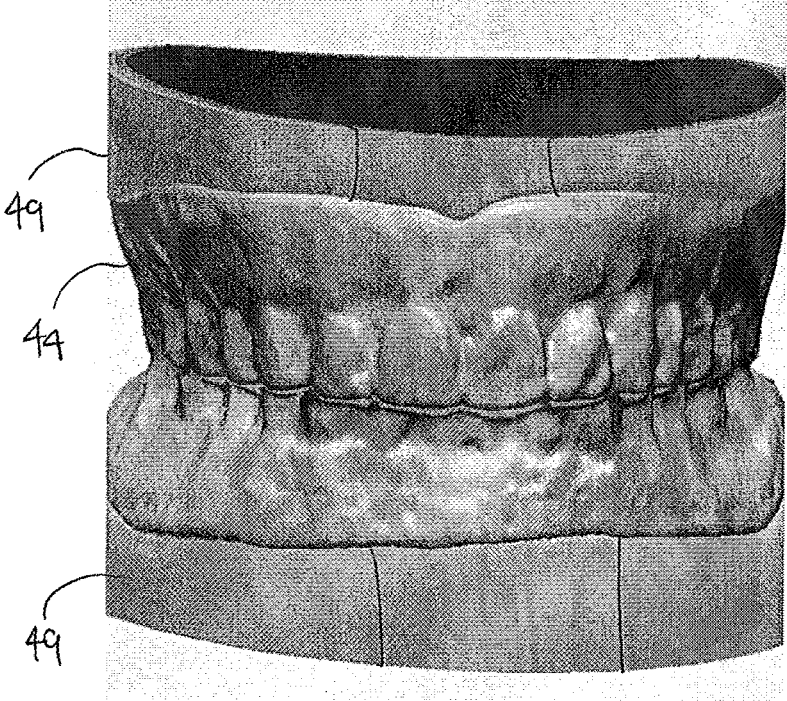
FIG. 9 is a processed image of current dentures for a patient as part of the present invention.
Figure 10:
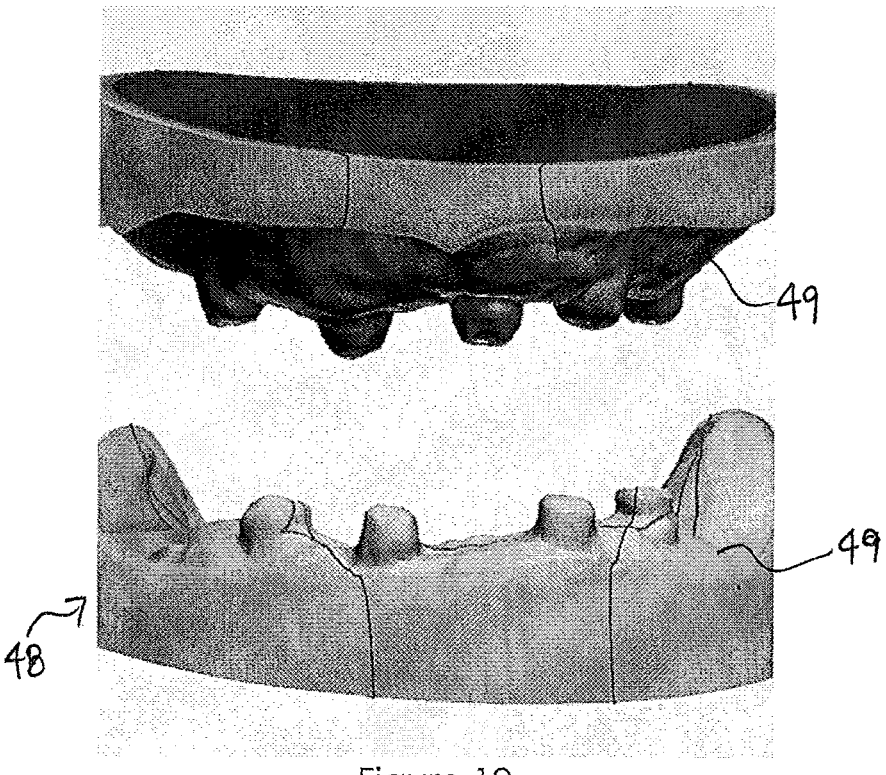
FIG. 10 is a processed image as part of the present invention.

As shown in FIG. 9, the initial three-dimensional rendering of the dentures is processed by the system to provide an initial digital model of the patient's upper and lower jaw structures 49 in relative position to one another. With properly oriented digital models of a patient's jaw surfaces 49 as shown in FIG. 10, along with a superimposable rendering of the initial prostheses 44 which allows alignment with the patient's smile images of both the existing denture 44 (FIG. 11) as well as the new denture tooth design 50 (FIG. 12). A prospective top 52 and bottom baseplate 54 adaptable to the patient's gum structure on the top and bottom of the oral cavity can then be created as shown in FIG. 13.

Figure 11:
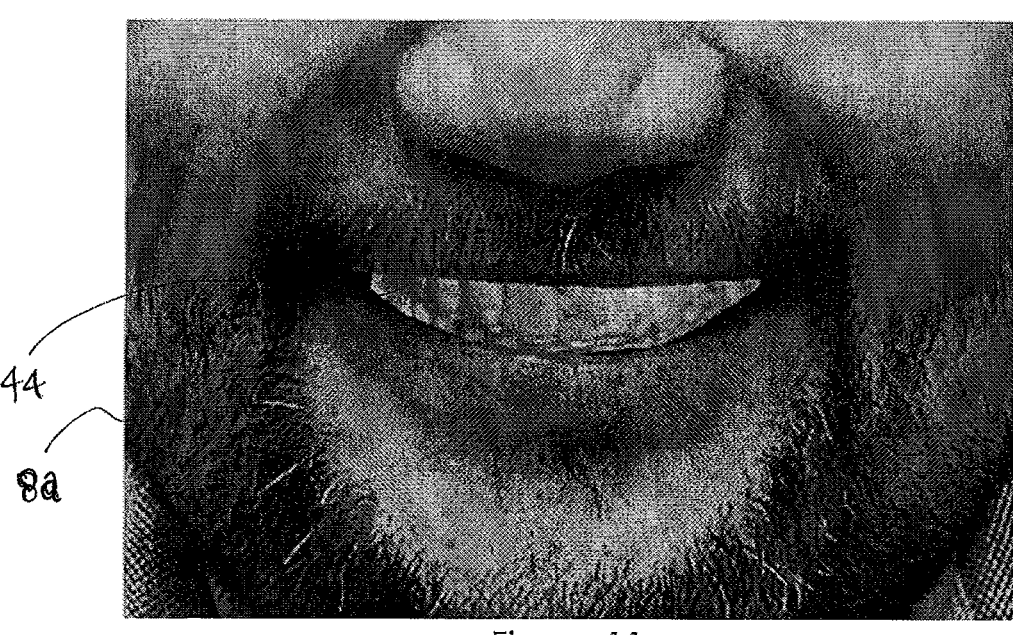
FIG. 11 is a processed image as part of the present invention.
Figure 12:
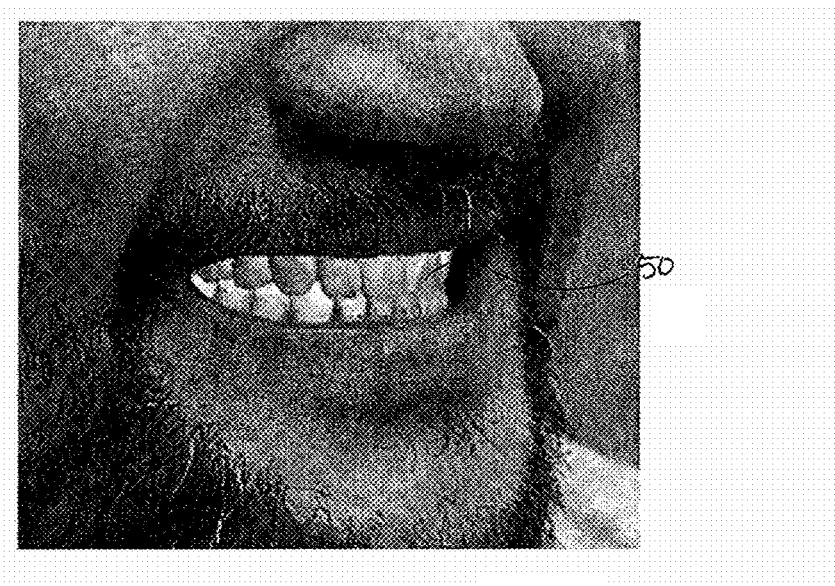
FIG. 12 is a processed image as part of the present invention.

As shown in FIGS. 11 and 12, the system utilizes patient image capture of the patient's face showing the teeth of the patient to process and provide new renderings for the creation of new artificial teeth 56. As shown in FIG. 11, the system processes the patient image capture of the patient's face to overlay the patient's initial three-dimensional rendering of the dentures within the patient's oral cavity. This composite rendering of the patient's face and patient's existing denture asset is then processed to create a set of artificial teeth for creation for the patient. As shown in FIG. 12, the system then overlays the proposed artificial teeth on the patient image capture of the patient's face in the oral cavity of the patient to allow the provider to determine if other adjustments need to be made.

Figure 13:
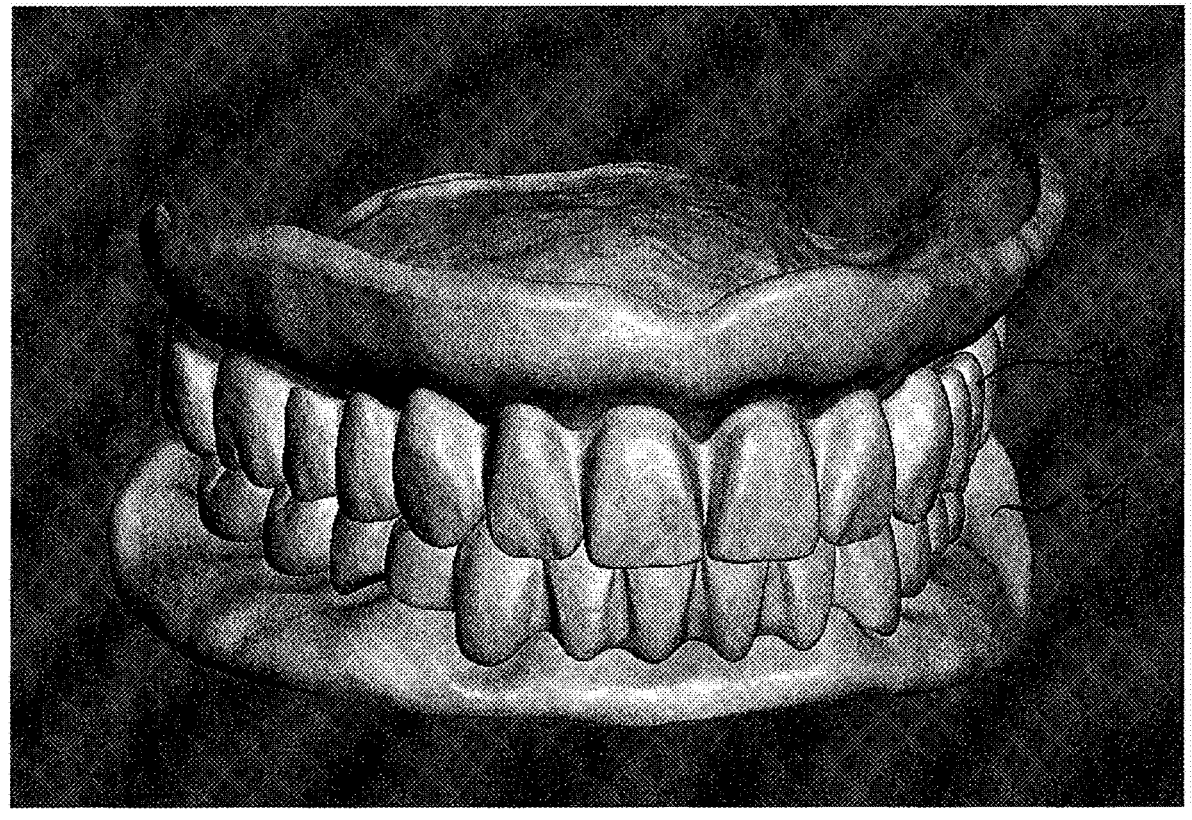
FIG. 13 is a processed image of digitally created teeth for the patient as part of the present invention.
Figure 14:
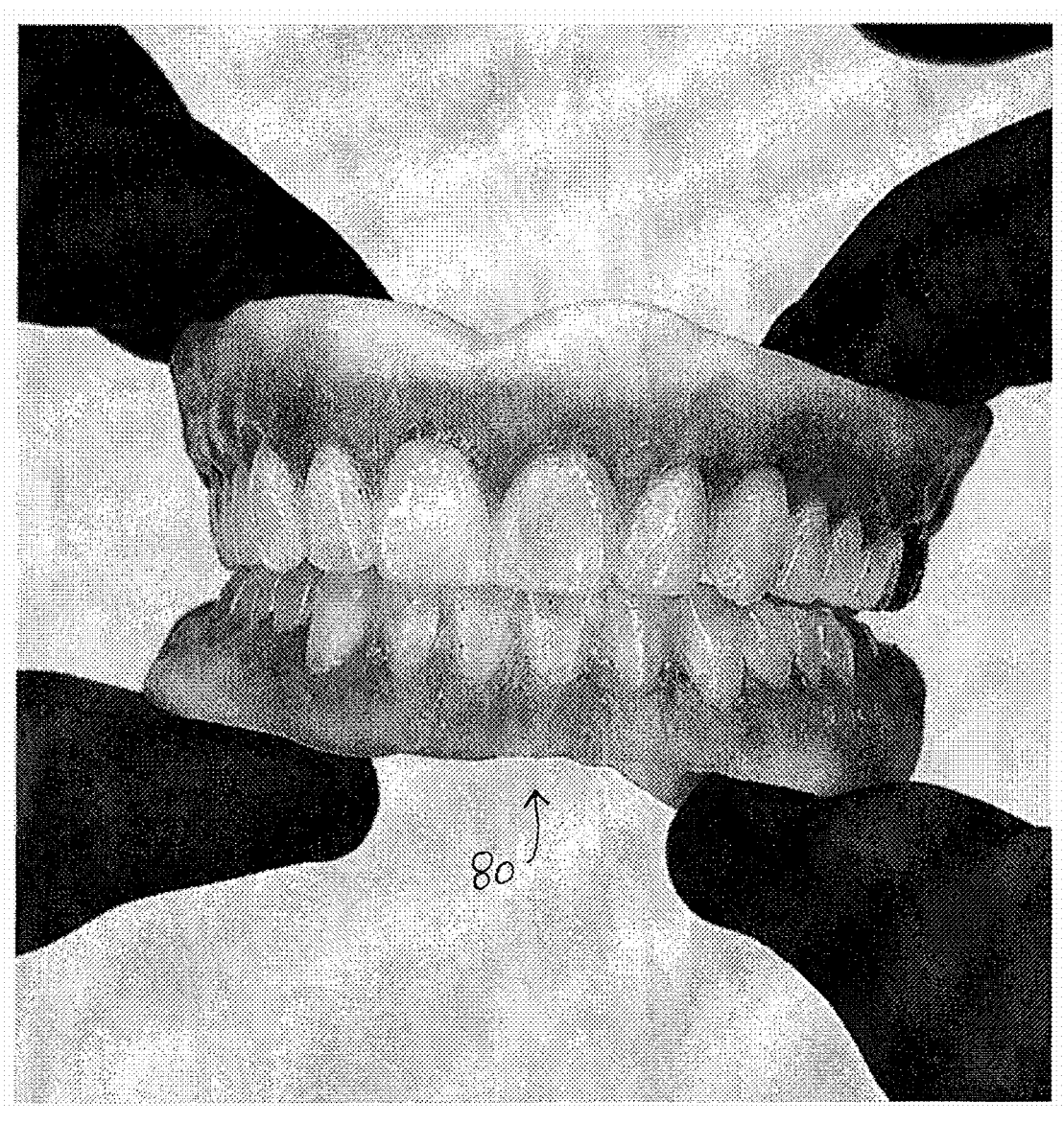
FIG. 14 is an image of digitally created dentures for the patient as part of the present invention.

As shown in FIG. 13, the top and bottom baseplate rendering is then used to orient the proposed artificial teeth to then provide a denture device. In a preferred embodiment, the system utilizes artificial intelligence tools to provide the processing for the steps shown in FIGS. 9-12.

With the digital smile design completed and treatment preview approved by patient and selected provider, the dental laboratory can prepare 8c initial dental assets for review by the provider and ship these assets to the provider for a try-in at the initial meeting.

The initial patient appointment now allows for the provider to directly review the digital images with the patient, complete the necessary clinical examination and direct diagnostics followed by a physical smile try-in using the asset(s) produced by the platform. In another embodiment, the initial patient appointment allows for the provider to provide the patient with a try-in set of dentures or new set of dentures for the patient. As can be appreciated by one in the art, this would remove wasted time at the provider office for both the provider and the patient. In yet another embodiment, the newly designed dentures can be sent directly to a patient for self-fitting and use without need for any dental clinic visits at all.

As shown in FIGS. 3-5 and FIGS. 13-14, initial dental assets 80 can be prepared by the provider or a dental laboratory for an initial try-in of the proposed correction. The initial dental assets 80 can be prepared based upon the calculated patient data from the uploaded patient image. As it relates to complete dentures, the try-in model 650 may be fabricated by a method including prototyping equipment such as three-dimensionally printing the baseplate 658, and artificial teeth 654 in situ in proper spatial orientation. There is a need to create the artificial teeth as separate from the baseplate and separable from each other as some teeth may need to be moved or repositioned during the try-in process in order to meet patient and/or provider satisfaction.

The process of three-dimensionally printing the artificial teeth 654 separate from the baseplate and separable from each other requires orientation of the print support framework 656 such that the neck of each artificial tooth 654 is spatially separate from the baseplate only minimally connected to the adjacent teeth at the interproximal contact point to allow the artificial teeth to be printed in situ but remain easily modifiable during the try-in appointment. As shown, the try-in is oriented such that the print support framework 656 connects to the back/top surface of each tooth and separately to the baseplate surface allowing minimal (if any) physical connection between the artificial teeth and the baseplate. The framework 656 is three-dimensionally printed in thin layers 660 to provide a temporary structure during printing and positioned in the manner described to allow for secondary application of thermoplastic interstitial material (i.e. baseplate wax) 664 to secure the artificial teeth to the baseplate in the proper spatial orientation so that the print support framework can be removed without affecting the position of the artificial teeth relative to the baseplate but still allow for usual and customary modifications of the try-in as would be possible with a traditional denture try-in. The orientation of the framework 656, i.e. connected to the back/top surface of each tooth, allows easy application of baseplate wax to the gap between the baseplate and the teeth from the facial/buccal side as it is opposite the build support connections. The addition of the baseplate wax relinks the separate baseplate and teeth and maintains their orientation relative to each other and allows the removal of the framework 656 without changing the orientation of the teeth relative to the baseplate.

As discussed above, the teeth are printed to allow functional movement of the teeth as deemed necessary by the dentist easily and quickly by simply warming the baseplate wax and modifying the tooth positions when the wax is soft, then recooling. This is helpful to achieve any necessary cosmetic and/or functional tooth corrections, i.e. shifting the upper teeth to align with facial/intraoral landmarks and also to achieve optimal bite posturing.

The wax compound 664 can be any color, however the use of a pink color mimics natural gingiva and is more pleasing for the try-in. Once the wax is in place, the scaffolding can be cut from the back of the teeth without movement of the individual teeth.

In another embodiment of the try-in assets 80 developed from the digital smile preview design, a physical model of the patient's teeth and oral tissues is created via rapid prototyping as a combined model of the dentition in its current state with the additional surfaces of the reconstructed teeth superimposed. From this physical model, a former (i.e. a silicone mold or a thermoplastic vacuum-formed shell) can be created which is used to apply removable tooth colored material (i.e. dental composite resin, impression material, etc.) directly to the pre-treatment dentition for direct visualization of the proposed treatment results. Often these surfaces are modified in size, shape, and/or position to ensure adequate coverage of the problematic, pre-treatment tooth surfaces with enough prosthetic preview material for successful direct visualization at the in-office smile try-in appointment.

In another embodiment of the try-in assets, if the digital treatment design surfaces are modified to achieve adequate material bulk on the necessary visible and functional surfaces of the pre-treatment dentition, a physical model of those teeth can be produced directly via prototyping equipment (3D printing or computer numeric control milling) as a stand-alone anatomic overlay (i.e. snap-on-smile). Given the materials and methods with which this type of try-in appliance can be produced, these could be sent home with the patient for extended trial review purposes or even shipped directly to the patient before the first clinical appointment with a dentist.

Unless otherwise stated, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein. It will be apparent to those skilled in the art that many more modifications are possible without departing from the inventive concepts herein.

All terms used herein should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. When a Markush group or other grouping is used herein, all individual members of the group and all combinations and subcombinations possible of the group are intended to be individually included. All references cited herein are hereby incorporated by reference to the extent that there is no inconsistency with the disclosure of this specification. When a range is stated herein, the range is intended to include all sub-ranges within the range, as well as all individual points within the range. When "about," "approximately," or like terms are used herein, they are intended to include amounts, measurements, or the like that do not depart significantly from the expressly stated amount, measurement, or the like, such that the stated purpose of the apparatus or process is not lost.

The present invention has been described with reference to certain preferred and alternative embodiments that are intended to be exemplary only and not limiting to the full scope of the present invention, as set forth in the appended claims.

The invention claimed is:

1. A method for generating scaled denture data for redesign and fabrication, the method comprising the steps of:
   a. providing a user interface of a platform;
   b. receiving through the user interface of the platform patient information comprising at least one digital media file of the patient, said at least one digital media file selected from the group consisting of an image file of an existing set of dentures placed proximate to a standardized household reference object having a known dimensionality and shape or a video file of an existing set of dentures placed proximate to a standardized household reference object having a known dimensionality and shape;
   c. processing the at least one digital media file of the patient;
   d. generating a three-dimensional digital model of the existing set of dentures based on the at least one digital image of the patient, wherein the standardized household reference object provides scaling data to calibrate denture dimensions for the three-dimensional digital model; and
   e. utilizing the three-dimensional model to create a digital preview of redesigned dentures; and
   f. fabricating a denture try-in model for the patient.

2. The method of claim 1, wherein the standardized household reference object is selected from the group consisting of an aluminum beverage can, a food can, or a packaged item of standardized dimension.

3. The method of claim 1, wherein said at least one digital media file of the patient is further selected from the group consisting of an image file, captured by a mobile device of the patient, of an existing set of dentures placed proximate to a standardized household reference object having a known dimensionality and shape or a video file, captured by a mobile device of the patient, of an existing set of dentures placed proximate to a standardized household reference object having a known dimensionality and shape.

4. The method of claim 1, wherein the video file comprises a circumferential recording of the denture relative to the standardized household reference object.

5. The method of claim 1, wherein the generated three-dimensional digital model is scaled by aligning denture features to the known dimensionality of the standardized household reference object.

6. A method of preparing dental treatment assets remotely, the method comprising:
   a. receiving at least one digital media file from the patient, said at least one digital media file selected from the group consisting of an image file of an existing set of dentures placed proximate a standardized household reference object having a known dimensionality and shape or a video file of an existing set of dentures placed proximate standardized household reference object having a known dimensionality and shape;
   b. constructing a scaled three-dimensional digital model of the existing set of dentures based on the at least one digital media file, using the standardized household reference object as a calibration reference;
   c. digitally modifying the scaled three-dimensional digital model of the existing set of dentures to design revised dentures;
      and groups;
   d. fabricating, prior to any clinical appointment, a dental asset selected from the group consisting of a denture try-in and a final denture prosthesis.

7. A method for providing dentures to a patient, the method comprising the steps of:
   a. receiving from the patient through a mobile device patient information comprising at least one digital media file of the patient, said at least one digital media file selected from the group consisting of an image file of an existing set of dentures placed proximate a household object for scale or a video file of an existing set of dentures placed proximate a household object for scale;

b. calculating patient information from the at least one digital media file of the patient; and c. generating a digital preview of a set of proposed dentures based on the at least one digital media file of the patient; and d. fabricating a denture try-in model for the patient.

\* \* \* \* \*